(12) United States Patent
Fima

(10) Patent No.: US 11,492,583 B2
(45) Date of Patent: Nov. 8, 2022

(54) PHYSICAL MANIPULATION OF TISSUE CULTURED TISSUE

(71) Applicants: MEATECH 3D, LTD., Rehovot (IL); THE IP LAW FIRM OF GUY LEVI, LLC, Wyckoff, NJ (US)

(72) Inventor: Sharon Fima, Kfar Hanagid (IL)

(73) Assignee: Steakholder Foods, LTD., Rehovot (IL)

( * ) Notice: Subject to any disclaimer, the term of this patent is extended or adjusted under 35 U.S.C. 154(b) by 0 days.

(21) Appl. No.: 17/762,316

(22) PCT Filed: Sep. 22, 2020

(86) PCT No.: PCT/US2020/052063
§ 371 (c)(1),
(2) Date: Mar. 21, 2022

(87) PCT Pub. No.: WO2021/055996
PCT Pub. Date: Mar. 25, 2021

(65) Prior Publication Data
US 2022/0267709 A1    Aug. 25, 2022

Related U.S. Application Data

(60) Provisional application No. 62/908,879, filed on Oct. 1, 2019.

(51) Int. Cl.
| | | |
|---|---|---|
| C12M 1/26 | (2006.01) | |
| B33Y 70/00 | (2020.01) | |
| B33Y 80/00 | (2015.01) | |
| A61L 27/36 | (2006.01) | |
| A61L 27/38 | (2006.01) | |
| C12M 1/12 | (2006.01) | |
| C12M 1/42 | (2006.01) | |
| C12M 1/34 | (2006.01) | |
| C12N 5/077 | (2010.01) | |
| A61K 38/00 | (2006.01) | |

(52) U.S. Cl.
CPC ......... C12M 33/00 (2013.01); A61L 27/3633 (2013.01); A61L 27/3804 (2013.01); B33Y 70/00 (2014.12); B33Y 80/00 (2014.12); C12M 25/14 (2013.01); C12M 35/04 (2013.01); C12M 35/08 (2013.01); C12M 41/00 (2013.01); C12N 5/0658 (2013.01); A61K 38/00 (2013.01); C12N 2513/00 (2013.01)

(58) Field of Classification Search
CPC ...... C12M 33/00; C12M 25/14; C12M 35/04; C12M 35/08; C12M 41/00; A61L 27/3633; A61L 27/3804; B33Y 70/00; C12N 5/0658; C12N 2513/00; A61K 38/00
See application file for complete search history.

(56) References Cited

U.S. PATENT DOCUMENTS

| | | |
|---|---|---|
| 2015/0351896 A1 | 12/2015 | D'Lima et al. |
| 2016/0145554 A1 | 5/2016 | Ingber et al. |
| 2018/0171304 A1 | 6/2018 | Beyer et al. |
| 2018/0313822 A1 | 11/2018 | Murphy et al. |

*Primary Examiner* — Titilayo Moloye
(74) *Attorney, Agent, or Firm* — Guy Levi; The IP Law Firm of Guy Levi, LLC

(57) ABSTRACT

The disclosure relates to methods, systems and compositions for physically manipulating a muscle tissue culture either mechanically, or manually, or both. Specifically, the disclosure relates to systems and methods of physically manipulating, either mechanically or manually, a resilient container of bioprinted tissue culture having non-random three dimensional cell structure by elongation, compression, torque and shear of the tissue culture.

19 Claims, 1 Drawing Sheet

PHYSICAL MANIPULATION OF TISSUE CULTURED TISSUE

CROSS REFERENCE TO RELATED APPLICATIONS

This patent application is a U.S. National Phase filing of commonly owned PCT Application No. PCT/US20/052063, filed Sep. 22, 2020, which is based on and claims the benefit of the filing date of U.S. Provisional Patent Application Ser. No. 62/903,879, filed Sep. 22, 2019, both which are incorporated herein by reference in their entirely.

BACKGROUND

The disclosure is directed to methods, systems and compositions for physically manipulating a muscle tissue culture either mechanically, or manually, or both. Specifically, the disclosure is directed to systems and methods of physically manipulating a resilient container of bioprinted tissue culture having non-random three dimensional cell structure over 4 dimensions.

In an effort to reduce the environmental impact of animal husbandry and to improve people's nutrition, as well as for various other incentives, there is a need for alternatives to animal meat for development of novel protein sources containing viable cells culture(s) that correspond to the three-dimensional (3D) tissue, for instance, muscle tissue. The use of the systems and methods, can affect differentiation, accelerate growth and increase nutrient efficiency ratios.

In addition, additive manufacturing approaches using Extra-cellular extrusion for scaffold fabrication for bone tissue engineering are typically used, but rigorous thermal or chemical treatments to the scaffolds during the fabrication process may adversely affect the efficacy of the resulting tissue growth. Moreover, stagnant growth conditions can adversely affect the quality of the meat produced from such tissue culture.

Therefore, the need exists for methods, systems and compositions for use in the bioprinting of precision-fabricated biostructures, such as skeletal muscles to be physically manipulated in a controlled manner.

SUMMARY

Disclosed, in various exemplary implementations, are systems and methods of manipulating a resilient container of bioprinted tissue culture having non-random three dimensional cell structure over 4 dimensions; torsion, elongation, compression, and shear and their combination, as well as exposure to osmotic and fluid stresses.

In an exemplary implementation, provided herein is a method of physically manipulating a tissue culture, implementable in a computerized system comprising: at least one resilient container operably coupled to a frame sized and configured to affect a predetermined regimen of stress and strain over at least one of four degrees of freedom on the at least one resilient container, and a central processing module (CPM) in communication with at least one processor and at least one non-volatile memory storage device having thereon a processor-readable media with a set of executable instructions, configured, when executed, to cause the at least one processor to: using a sensor array, receive physical data characteristic of the tissue culture; and based on the data, physically manipulate the at least one resilient container, the method comprising: loading the tissue culture into the at least one resilient container; and at predetermined intervals, based on the physical data characteristic of the tissue culture, affect at least one of stress, and strain on the at least one resilient container.

In another exemplary implementation, exemplary implementations of the tissue cultures provided herein is transferred to the resilient container are formed through a method of bioprinting using a 3D inkjet printer comprising: providing a 3D inkjet printer, the printer having: a library to store printer operation parameters; at least one processor in communication with the library; a non-volatile memory storage device storing a set of operational instructions for execution by the at least one processor; a micromechanical inkjet print head or heads in communication with the at least one processor and with the library; and a print head or, heads' interface circuit in communication with the library, the memory and the micromechanical inkjet print head or heads, the library configured to provide printer operation parameters specific for a substantially 2D layer or portion of a specific layer; pre-processing Computer-Aided Design/Computer-Aided Manufacturing (CAD/CAM) generated information associated with the bioprinted tissue culture to be fabricated, thereby obtaining a plurality of vector data models and/or bitmaps, each vector data model and/or bitmap specific for a predetermined layer or their interface and/or cross section and/or a portion thereof; loading the plurality of bitmaps and/or vector data models processed in the step of pre-processing onto the library; and using the library, instructing the processor to print the predetermined layer, its interface and/or a portion thereof in a predetermined order.

In an exemplary implementation, the system further comprises a bioprinting module, the module having at least one microprocessor in communication with: a non-volatile storage device having thereon a microprocessor-readable medium with set of executable instructions configured to, when executed, to cause the at least one microprocessor to execute a method of inkjet bioprinting; and an image library corresponding to a two dimensional (2D) layer of at least one of cells, scaffolding, and connective tissue within the biostructure having predetermined 3D pattern of cells therein; a first dispensing print head in communication with the microprocessor having: at least one aperture, a first bio-ink reservoir, and a first dispenser configured to dispense the first bio-ink through the aperture, wherein the first bio-ink is a composition comprising viable cells suspended in a bio-compatible dispersing medium and/or bio-compatible polymer, and/or monomer, and/or oligomer; a second dispensing print head in communication with the microprocessor having: at least one aperture, a second bio-ink reservoir, and a second dispenser configured to dispense the second bio-ink through the aperture, wherein the second bio-ink is a composition bio-compatible compounds suspended in a bio-compatible dispersing medium and/or bio-compatible polymer, and/or monomer, and/or oligomer; a third dispensing print head in communication with the microprocessor having: at least one aperture, a third bio-ink reservoir, and a third dispenser configured to dispense the third bio-ink through the aperture, wherein the third bio-ink comprises means for functionalizing the bio-compatible polymer, monomer, or oligomer; and a conveyor in communication with the microprocessor, operably coupled to each of the first, the second, and the third dispensing print heads.

For example, a first bio-ink can comprise a dispersing medium (e.g., Eagle Medium) with a first polymer, monomer or oligomer without any cells suspended in it, which can be used to form the scaffolding for the tissue culture. The first print head may be associated with a dedicated functionalizing print head which can be used to stiffen the polymer to a desired degree. The scaffolding can be printed and configured to form lumens with spaced openings. A second print head with a second bio ink can be used, wherein the second bio-ink can comprise dispersing medium with cells which has been triggered, or otherwise manipulated to undergo a specific differentiation and/or alternatively, cells and either the same or different biocompatible polymer, monomer or oligomer, associated with another functionalizing print head. A third print head can be used with a third bio-ink comprising a dispersing medium with triggering compounds therein and either the same or different biocompatible polymer, monomer or oligomer. Another (fourth) print head can be used with a fourth bio-ink, comprising dispersing medium with viable cells, associated with a dedicated functionalizing print head. Adding and/or removing of the various print head can be done based on the printed tissue culture.

BRIEF DESCRIPTION OF THE FIGURES

For a better understanding of the systems, and methods for improving connectivity of embedded integrated circuits, with regard to the exemplary implementations thereof, reference is made to the accompanying examples and figures, in which.

DETAILED DESCRIPTION

Figure 1:
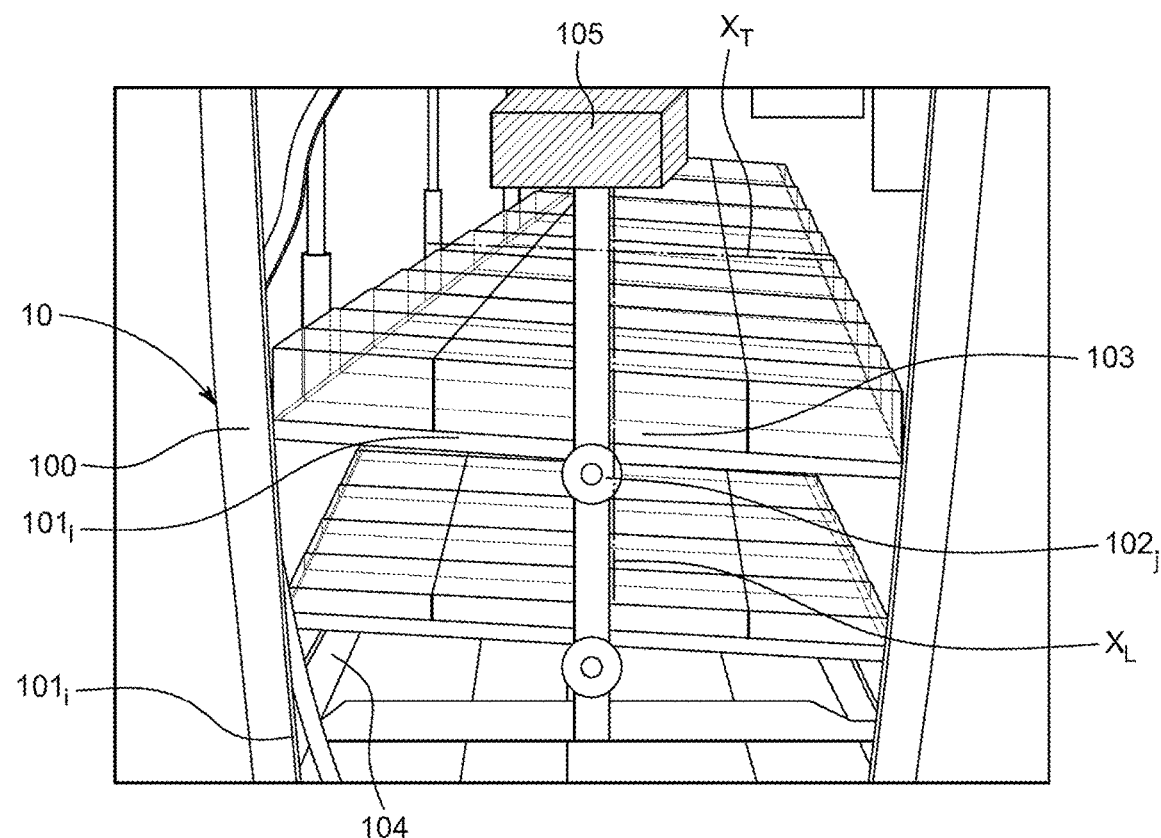
FIG. 1, is a perspective illustration of an exemplary implementation of the frame holding trays operating as a resilient container. configured to induce elongation, compression, torsion and shear unto the resilient container (e.g., trays)

Provided herein are exemplary implementations of systems and methods of manipulating a resilient container of bioprinted tissue culture having non-random three dimensional cell structure over 4 dimensions. The exemplary implementations described are configured to improve differentiation and growth of the tissue cultures, resulting in edible biostructures having a predetermined three dimensional structure that emulate meat for food consumption.

Skeletal muscle comprises a large percentage of edible meat. Even in intact muscle tissue, small physically induced tears, and lacerations heal and actually been reported to strengthen the muscle tissue. Furthermore, applying external contractile forces on muscle mass can upregulate certain factors, such as for example, the activation of a protein kinase referred to as the mechanistic target of rapamycin (mTOR). Once formed, striated appearance of muscle is the result of cylindrically shaped myofibrils, which are comprised of sarcomeres units separated by Z discs (lines, hence the striated appearance). Using the systems and methods disclosed herein, can promote alteration to the connective tissue and the myofibrillar protein networks.

Accordingly and in an exemplary implementation, provided herein is a method of physically manipulating a tissue culture, implementable in a computerized system comprising: at least one resilient container operably coupled to a frame sized and configured to affect a predetermined regimen of stress and strain over at least one of four degrees of freedom on the at least one resilient container, and a central processing module (CPM) in communication with at least one processor and at least one non-volatile memory storage device having thereon a processor-readable media with a set of executable instructions, configured, when executed, to cause the at least one processor to: using a sensor array, receive physical data characteristic of the tissue culture; and based on the data, physically manipulate the at least one resilient container, the method comprising: loading the tissue culture into the at least one resilient container; and at predetermined intervals, based on the physical data characteristic of the tissue culture, affect at least one of stress, and strain on the at least one resilient container.

The tissue cultures described herein may be tissue substitute including but not limited to a bone cartilage, liver, epithelial, muscular, fatty tissue and the like, or other tissue substitute for either a portion of a tissue or an entire tissue and/or organ. The tissue culture, or its corresponding matrix, may have dimensions which may be customized for a particular application (e.g., fish cross section, T-Bone steak and the like). The tissue culture may be used in culturing cells in-vitro, in a separate bio reactor whereby the device for manipulating the tissue culture, accommodated in the resilient containers, is forming a part of that bioreactor. In other words, once the tissue is bioprinted, the culture is transferred to the resilient containers as part of the bioreactor, where, in addition to providing nutrients and other chemical and biological agents, the systems provided are physically manipulating the tissues to increase differentiation and adjust the physical properties of the extracellular matrix (ECM).

The resilient containers can be trays formed of an elastomeric material. Example of such elastomeric material can be, for example, butadiene, natural rubber, synthetic rubber, silicone, urethane, neoprene, polyester, di-cyclopentadiene monomer, expanded polypropylene, and their combination. In addition, the term "resilient" in the context of the disclosure refers to such flexible features as generally returning to an initial general shape without permanent deformation following the application of elongation forces, compression forces, torsion and shear. Accordingly, and in another exemplary implementation, the resilient containers define a longitudinal axis, and a transverse axis, and the elongation forces, compression forces, torsion and shear are applied along at least one of: the longitudinal axis ($X_L$), and transverse axis ($X_T$).

Additionally or alternatively, the resilient containers can be bladders made of elastomeric material containing the tissue culture (bioprinted using the bioprinting module disclosed). In general, the resilient container(s) disclosed are configured to contain the tissue culture in such a way that will transfer elongation, contractile (compression), torsion and shear forces from the container onto the tissue culture.

Figure 2A:
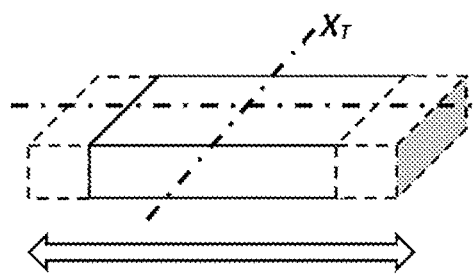
FIGS. 2A-2D illustrate the physical forces of stress and strain impose by elongation (2A), compression (2B), torsion (2C) and shear (2D).
Figure 2B:
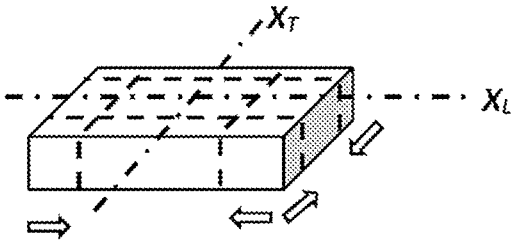
Figure 2C:
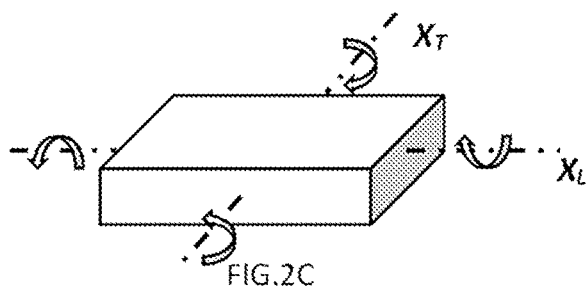
Figure 2D:
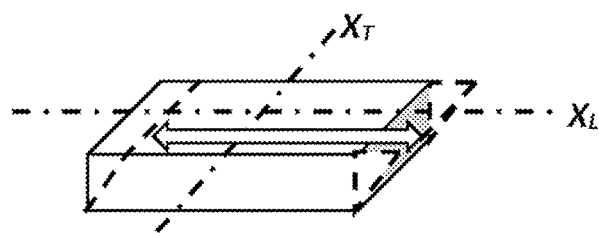

In the context of the disclosure, the term "elongation" refers both to strain and stress imposed on the tissue culture by manipulating the resilient container, caused by stretching the container along at least one of: the longitudinal, and transverse axes, by, for example, between 1% and 25% relative to the longitudinal, and transverse axes original length (see e.g., FIG. 2A). Similarly, applying compressive force is intended to mean opposed forces (e.g., by the tissue culture) applied to either axis (longitudinal and/or transverse, see e.g., FIG. 2B) of the resiliently compressible container so as to compress the tissue culture. Likewise, torsion, in the context of the disclosure refers to any force exerted in any direction including but not limited to compression rotation, extension rotation, torque and or force applied movement in any direction, leading to a twisting motion in opposite direction (see e.g., FIG. 2C). Also, "shear" in the context of this disclosure refers to the displacement of any layer of the tissue culture relative to another layer (see e.g., FIG. 2D). Accordingly and in an exemplary implementation, the four degrees of freedom applied by the physical manipulation device disclosed herein, are configured to compress, elongate, shear and apply torque to the tissue culture in the at least one resilient container and thereby, the tissue culture contained therein.

The systems, devices and methods described herein can further comprise a sensor array, array configured to provide physical characteristic data from the tissue culture. It is noted, that the sensor array can provide data on the growth, differentiation, and development of the tissue culture in addition to its physical characteristics. For example, the physical characteristic can be at least one of: viscosity, density, weight, opacity, specific volume, relative water activity (Aw), pH, tensile strength, and compressive strength. In an exemplary implementation, the set of executable instructions is configured, when executed, to receive the data from the sensor array and adjust, modify or otherwise control the regimen used to physically manipulate the resilient containers, for example, by changing degree and frequency of manipulation using the combination of at least one of compression, elongation, shear and torsion of the content of the resilient containers.

To generate the data, the system can therefore comprise a sensor array comprising at least one of a timer, a viscometer, a load cell, an actinic radiation source, a camera, and a hygrometer. Moreover, the systems and devices disclosed herein further comprises means for affecting at least one of: osmotic stress, and fluid stress. In the context of the disclosure, the term "osmotic stress" refers to culture conditions wherein the osmolarity is sufficiently higher than that needed for the maximum rate of increase in numbers of cells so as to result in a measurable different in one or more cellular traits (such as rate of growth) and/or the extracellular matrix. Similarly, fluid stress refers to the stress induced by the flow of the tissue culture, for example, by causing the tissue to flow through an orifice or other opening in the resilient container. For example, the means for affecting osmotic stress comprises contacting the at least one resilient container with a membrane containing an agent (e.g., salt solution with various salt concentrations) with a higher chemical potential than the tissue culture at any given time, while the means for affecting fluid stress comprises a tube affecting fluid communication between two resilient containers.

In addition, the resilient containers can be coated internally, so as to promote adhesion (in other words, wetting) of the tissue culture onto the resilient container. The coating can be, for example PEGilated tripeptides, such as PEG-Arg-Gly-Asp (RGD) and the like tripeptides that are capable of interacting with tissue culture cells' adhesion proteins, for example (cyclo Arg-Gly-Asp-d-Phe-Lys (cRGDfK) or cyclo Arg-Gly-Asp-d-Phe-Cys (cRGDfC)).

Furthermore, the methods and systems disclosed further comprise admixing biocompatible pellets to the at least one resilient container, the pellets configured to impose a predetermined shape to at least a portion of the tissue culture, The pellets can be an integral part of the container and create various pathways such that during manipulation of the resilient container (either mechanically, or manually), various types of flow stresses are imposed. Likewise, different surface coating can prevent wetting of the tissue culture, thus imposing formation of drops or otherwise create spherical portions of the tissue.

As indicated, the inkjet bioprinting module is configured to provide the tissue culture. The term "bioprinting" refers to a process of making specific type or several types of native or manipulated cells configured to form the edible tissue analog by depositing scaffolding (matrix) material mixed with cells and other bio-inks using inkjet printer having drop-on-demand capabilities. Likewise, the term "forming" (and its variants "formed", etc.) refers in an exemplary implementation to pumping, injecting, pouring, releasing, displacing, spotting, circulating, nebulizing, spaying, inkjetting, jetting, or otherwise placing a fluid or material (e.g., the myocytes-containing bio-ink) in contact with another material (e.g., the scaffold, connective tissue or another myocytes layer) using any suitable inkjet printing method. In an exemplary implementation, "forming" refers to the assembly of the 3D tissue culture itself from its underlying 2D layer images, which, in another exemplary implementation are derived from various raster images (e.g., .dcm) and/or vector data models.

Moreover, in the context of the current disclosure, the term "scaffold", or "biocompatible scaffolding" refers in an exemplary implementation to an engineered platform having a predetermined three dimensional structure, which mimic the 3D environment of the natural extracellular matrix (ECM), provide short term mechanical support of the tissue culture, and provide an increased surface area for cells adhesion, proliferation, migration, and differentiation, eventually leading to accelerated tissue formation. Additionally or alternatively, "scaffolding" refers to a fabricated systems of conduits, sized adapted configured, once printed, to maintain fluid communication within the growing tissue culture to nutrients, buffer fluids, functionalizing fluids and other similar functional liquids. As indicated, the scaffold can also be a composite scaffold. A "composite scaffold" refers to a scaffold platform which is engineered in order to support colonization and/or proliferation of two or more tissue types which together comprise a "heterogeneous tissue". For example, the systems and methods described herein can be used to form a composite scaffold comprising a first 3D, chondrocytes-embedded tissue culture (e.g., tissue, organ, tissue scaffold, connective tissue) for supporting formation of a first tissue type (e.g., cartilage) thereupon and a second 3D, myocytes-embedded tissue culture (e.g., muscle tissue, meat replacement, tissue scaffold) for supporting formation of a second tissue type thereupon (e.g., muscle).

In the context of the disclosure provided herein, the term "dispenser" is used to designate the dispensing print-head from which the inkjet ink drops are dispensed. The dispenser can be, for example an apparatus for dispensing small quantities of liquid including micro-valves, piezoelectric dispensers, continuous-jet print-heads, boiling (bubble-jet) dispensers, pumps and others dispensing means affecting the temperature and properties of the fluid and/or bio-ink flowing through the dispenser.

Formulating the first inkjet composition, may take into account the requirements, if any, imposed by the dispensing print head and the surface characteristics (e.g., hydrophilic or hydrophobic, and the surface energy of and optionally provided substrate). For example, using inkjet with a piezo electric dispensing print head, the viscosity of either the first bio-ink and/or the second bio-ink (measured at printing temperature) can be, for example, not lower than about 5 cP, e.g., not lower than about 8 cP, or not lower than about 10 cP, and not higher than about 30 cP, e.g., not higher than about 20 cP, or not higher than about 15 cP. The first bio-ink, can be configured (e.g., formulated) to have a dynamic surface tension (referring to a surface tension when an ink-jet bio-ink droplet is formed at the dispensing print-head aperture) of between about 25 mN/m and about 35 mN/m, for example between about 29 mN/m and about 31 mN/m measured by maximum bubble pressure tensiometry at a surface age of 50 ms and at 25° C. The dynamic surface tension can be formulated to provide a contact angle with the substrate of between about 1 deg. centigrade and about 166 deg. centigrade, for example, between about 20 deg. centigrade and about 130 deg. centigrade, or between about 35 deg. centigrade deg. centigrade and about 90 deg. Likewise, contact angles between layers and between various bio-inks can be formulated to provide either wetting or form discrete drops on the surface as needed.

In an exemplary implementation, the first bio-ink composition used to form the layer of cells, and/or the second bio-ink comprising a composition comprising bio compatible and/or manipulation triggering compounds can comprise biocompatible polymers, for example; PEGilated-methacrylate, PEG-dimethacrylate (PEGDMA), carrageenan, poly(lactic) acid, poly(lactic-co-glycolic acid), (poly(lysine)), their methacrylate conjugates, co-polymers, interpenetrating networks or a composition comprising one or more of the foregoing.

The term "biocompatible polymer" refers to any polymer which when in contact with the cells, tissues or body fluid of an organism; does not induce adverse effects such as immunological reactions and/or rejections and the like. In addition, the first and/or second bio-ink used in the methods and systems described herein can be a biodegradable polymer, referring in an exemplary implementation to any polymer which can be degraded in the physiological environment such as by proteases. Examples of biodegradable polymers are; collagen, fibrin, hyaluronic acid, polylactic acid (PLA), polyglycolic acid (PGA), polycaprolactone (PCL), polydioxanone (PDO), trimethylene carbonate (TMC), polyethyleneglycol (PEG), alginate, chitosan or mixtures thereof.

In an exemplary implementation, a carrageenan hydrocolloid can be used in the first and/or second bio ink, for example kappa carrageenan (κ-CA) and functionalizing comprises heating and using the third print head—depositing ionic solution comprising KCl, $CaCl_2$, and their combination. Likewise, the first bio-ink composition comprises poly(ethylenoxide)-methacrylate (PEODMA) and functionalizing comprises exposure to electromagnetic radiation (EMR). The PEO can be, for example Poly(ethylenglycol). The physico-chemical properties of the first and/or second bio-inks can be controlled by varying for example molecular weight, chemical composition, the amount and type of functionalizing agent used and the degree of functionalization, which modifies their mass transport properties, physico-chemical properties and biological properties. Also, poly(ethylene glycol)-diacrylate (PEG-DA) hydrogels have been shown to be compatible in vivo with porcine islet cells and poly(ethylene glycol)-dimethacrylate (PEG-DMA) hydrogels to be compatible with chondrocytes. By varying the suspension polymer used in the first and/or second bio-ink; bio-compatible, or bio-mimetic polymer, the viscosity of the 3D pattern of the embedded cells can be maintained and configured to either prevent colonization and/or manipulation, or alternatively optimize and accelerate manipulation. The biocompatible polymer can also be Chitosan or PEGilated Chitosan where the PEGilated Chitosan is conjugated to methyl methacrylate, or dimethyl methacrylate (e.g. CEG-MA and or CEG-DMA).

Specifically with regard to myocytes, and in an exemplary implementation, the scaffolding structure can be formed from biocompatible polymers configured to affect differentiation, growth and bioactivity of the myocytes or any pluripotent stem cells. These biocompatible polymers can be, for example, at least one of PGA, gelatin, alginate, and collagen, which are further conjugated or substituted with Arginylglycylaspartic acid (RGD peptide). For example, the tissue culture's scaffolding can be, for example, crosslinked, multilayer, electrospun gelatin nanofibers, printed and functionalized (e.g., crosslinked) using the systems disclosed herein. Moreover, the first bio-ink can comprise satellite cells and/or other myogenic progenitor cells (e.g., muscle precursor cells (MPCs)) while functionalizing can further comprise using electrostimulation of the scaffold.

As indicated, the first and/or second bio-inks can be used to form 3D cell-embedded tissue culture (e.g., tissue, organ, tissue scaffold, connective tissue) with bio-compatible compositions from PEG-DMA monomers suspended in aqueous solution and be gelled by radical polymerization in the presence of a photoinitiator. The polymerization reaction starts when the solution is exposed to UV light. Each PEG-DMA monomer has two methacrylate groups which can react with up to two other methacrylate groups to make covalent bonds in other words, cross linking forming a covalently crosslinked branched network. Accordingly, by varying PEG chain length, the concentration of the photoinitiator (e.g., Phenylglyoxylate, benzophenone) duration and wavelength of the EMR exposure, the final compressive modulus of the tissue culture support layer, or the predetermined cells' suspending layer can be optimized.

In an exemplary implementation, the apparent viscosity of the first, second, or third bio-ink composition(s), can each be (before functionalizing) between about 0.1 and about 30 cP·s (mPas) at the printing temperature, for example the final ink formulation can have a viscosity of 8-12 cP·s at the working temperature, which can be controlled. For example, cells' dispersion, solution, emulsion, suspension, hydrogel or liquid composition comprising the foregoing, or the second bio-ink comprising suspended cells can each be between about 5 cP·s and about 25 cP·s, or between about 7 cP·s and about 20 cP·s, specifically, between about 8 cP·s and about 15 cP·s.

In an exemplary implementation, the volume of each droplet of the first and/or second and/or third bio-ink(s), can range of about 5 pL to about 450 picoLiter (pL), for example between about 50 pL and about 150 pL, depended on the printer parameters and the properties of the ink. The waveform to expel a single droplet can be a 10V to about 170 V pulse, or about 16V to about 90V, and can be expelled at frequencies between about 1 kHz and about 500 kHz.

In addition, polymer concentration (e.g., PEGDMA, Chitosan), although being the same in the first and second bio-ink (in other exemplary implementation, the suspending polymer can be different), can vary in concentration between the inks, thus providing different physico-chemical characteristic to the hydrogel structures formed. In an exemplary implementation, after curing (in other words, solidifying, and/or otherwise functionalizing the matrix), the scaffold support pattern formed can exhibit compressive modulus (in other words, the ratio between the load and strain needed to achieve irreversible deformation of the gel), of no less than 0.5 MPa, for example, between 0.5 and 1.5 MPa or between about 0.6 MPa and 1.0 MPa. Other compressive moduli can be designed for the tissue culture itself, which can be between about 0.08 MPa and about 1.0 MPa.

As indicated, provided herein is a computerized bioprinting method for forming a composite tissue culture (e.g., tissue, organ, tissue scaffold, connective tissue, and their combination) having predetermined 2d and/or 3D pattern of cells (e.g., one or more of endothelial cells, muscle cells, fibroblast cells, mesothelial cells, pericyte cells, monocyte cells, plasma cells, mast cells, adipocyte cells, chondrocyte cells, or a cell population cultured from a specific cell type) therein, the method comprising: providing an inkjet printing system in communication with a microprocessor coupled to a non-volatile storage device storing a processor readable media with an executable set of instructions configured, when executed, to cause the (at least one, but potentially more) processor(s) to perform the method, as well being in communication with a database having a library of 2D images of the various layers to be printed, the system comprising: a first dispensing print head having: at least one aperture, a first bio-ink reservoir, and a first dispenser configured to dispense the first bio-ink through the aperture, wherein the first bio-ink is a composition comprising cells (or a cell composition comprising one or more of the cells provided herein), suspended in a bio-compatible dispersing medium, a bio-compatible polymer, monomer, or oligomer and a dispersing medium; a second print head having: at least one aperture, a second bio-ink reservoir, and a second dispenser configured to dispense the second bio-ink through the aperture, wherein the second bio-ink is a composition comprising extracellular matrix (ECM) composition, such as, at least one of: growth promoting, growth sustaining, and growth determining compounds, suspended in a bio-compatible dispersing medium and/or a bio compatible polymer, monomer, or oligomer; a third print head having: at least one aperture, a third bio-ink reservoir, and a third dispenser configured to dispense the third bio-ink through the aperture, wherein the third bio-ink comprises means for functionalizing the bio-compatible polymer, monomer, or oligomer; and a conveyor, operably coupled to the first print head, the second print head and to the third print head; following the uploading of a 2D image of a first layer or portion thereof, using the first inkjet print head, forming a first layer of cells' pattern or a portion of the first layer; using the third print head, functionalizing the first layer of cells pattern; using the second inkjet print head, forming a first layer of predetermined pattern of the second bio-ink composition or portion thereof; and using the third print head, functionalizing the first layer of predetermined pattern of the second bio-ink; using the first inkjet print head, forming a second layer of cells pattern on and/or adjacent to the first layer of cells pattern and/or the first layer of predetermined pattern of the second bio-ink composition or a portion of the first layer; and functionalizing the second layer of cells' pattern and in addition, using the second inkjet print head, forming a second layer of predetermined pattern of the second bio-ink on and/or adjacent to the first layer of cells pattern and/or the first layer of predetermined pattern of the second bio-ink composition; and functionalizing the second layer of predetermined pattern of the second bio-ink or a portion thereof.

Likewise, the predetermined 3D pattern of the second bio-ink, embedded in the layer of cells and tissue culture described herein, can be non-random. In other words, the cell-laden tissue culture has a substantial variation in the spatial distribution and/or density of the cells, forming a predetermined 2D (gleaned for example, from MRI and/or CT images converted to raster and/or vector data models and converted to inkjet printing instructions) and/or 3D pattern of cells. For example, the predetermined three dimensional pattern of the second bio-ink can be configured to; accelerate cell adhesion, retain native growth of the cells, and/or organ and/or tissue and other similar functions. Furthermore, the 3D scaffolding support and the cell-laden scaffold can be configured to emulate an edible animal tissue, for example, a muscle tissue and can comprise, for example, myocytes, satellite cells and other myogenic cells dispensed in the first bio-ink, while nanofibers of at least one of, PCL and collagen are dispensed in the second bio-ink, with the third bio-ink comprising RGD peptide.

Moreover, the second bio-ink, can further comprise other additives that affect colonization, proliferation, adherence, inhibit apoptosis or other manipulation of the cells, retain native growth of the cells, and/or organ and/or tissue and other similar functions. Accordingly and in an exemplary implementation, the second bio-ink used in the methods, systems and compositions for use in the direct inkjet bioprinting of a composite tissue culture (e.g., tissue, organ, tissue scaffold, connective tissue), can further comprise: cells manipulation triggering compounds, (for example, epidermal growth factor (EGF), basic fibroblast growth factor (bFGF), bone morphogenic protein (BMP), insulin-like growth factor (IGF), glucoseaminoglycan (GAG), Transforming growth factor (TGF) or signaling compound composition comprising the foregoing), as well as therapeutically effective compounds, antimicrobial compounds, immunosuppressing compounds and the like.

The term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

All ranges disclosed herein are inclusive of the endpoints, and the endpoints are independently combinable with each other. "Combination" is inclusive of blends, mixtures, alloys, reaction products, and the like. The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the container(s) includes one or more container). Reference throughout the specification to "one exemplary implementation", "another exemplary implementation", "an exemplary implementation", and so forth, when present, means that a particular element (e.g., feature, structure, and/or characteristic) described in connection with the exemplary implementation is included in at least one exemplary implementation described herein, and may or may not be present in other exemplary implementations. In addition, it is to be understood that the described elements may be combined in any suitable manner in the various exemplary implementations.

All ranges disclosed herein are inclusive of the endpoints, and the endpoints are independently combinable with each other. Furthermore, the terms "first," "second," and the like, herein do not denote any order, quantity, or importance, but rather are used to denote one element from another.

Likewise, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. For example, "about" as used herein mean a reasonable amount of deviation of the modified term such that the end result is not significantly changed. These terms of degree should be construed as including a deviation of at least ±5% or at least ±10% of the modified term if this deviation would not negate the meaning of the word it modifies.

Accordingly and in an exemplary implementation, provided is a method of physically manipulating a tissue culture, implementable in a computerized system comprising: at least one resilient container operably coupled to a frame sized and configured to affect a predetermined regimen of stress and strain over at least one of four degrees of freedom (DOF) on the at least one resilient container, and a central processing module (CPM) in communication with at least one processor and at least one non-volatile memory storage device having thereon a processor-readable media with a set of executable instructions, configured, when executed, to cause the at least one processor to: using a sensor array, receive physical data characteristic of the tissue culture; and based on the data, physically manipulate the at least one resilient container, the method comprising: loading the tissue culture into the at least one resilient container; and at predetermined intervals, based on the physical data characteristic of the tissue culture, affect at least one of stress, and strain on the at least one resilient container, wherein (i) the system further comprises an ink jet bioprinting module having at least one microprocessor in communication with: a non-volatile storage device having thereon a microprocessor-readable medium with set of executable instructions configured to, when executed, to cause the at least one microprocessor to execute a method of inkjet bioprinting; and an image library corresponding to a two dimensional (2D) layer of at least one of cells, scaffolding, and connective tissue within the biostructure having predetermined 3D pattern of cells therein; a first dispensing print head in communication with the microprocessor having: at least one aperture, a first bio-ink reservoir, and a first dispenser configured to dispense the first bio-ink through the aperture, wherein the first bio-ink is a composition comprising viable cells suspended in a bio-compatible dispersing medium and/or bio-compatible polymer, and/or monomer, and/or oligomer; a second dispensing print head in communication with the microprocessor having: at least one aperture, a second bio-ink reservoir, and a second dispenser configured to dispense the second bio-ink through the aperture, wherein the second bio-ink is a composition bio-compatible compounds suspended in a bio-compatible dispersing medium and/or bio-compatible polymer, and/or monomer, and/or oligomer; a third dispensing print head in communication with the microprocessor having: at least one aperture, a third bio-ink reservoir, and a third dispenser configured to dispense the third bio-ink through the aperture, wherein the third bio-ink comprises means for functionalizing the biocompatible polymer, monomer, or oligomer; and a conveyor in communication with the microprocessor, operably coupled to each of the first, the second, and the third dispensing print heads, wherein (ii) the four degrees of freedom are configured to compress, elongate, shear and apply torque to the tissue culture in the at least one resilient container, (iii) the system further comprises a sensor array configured to provide physical characteristic data from the tissue culture, wherein (iv) the physical characteristic is at least one of: viscosity, density, weight, opacity, specific volume, relative water activity, pH, tensile strength, and compressive strength, wherein (v) the sensor array comprises at least one of: a timer, a viscometer, a load cell, an actinic radiation source, a camera, and a hygrometer, wherein (vi) the tissue culture is configured to emulate a bovine muscle tissue, a porcine muscle tissue, an avian muscle tissue, a gnatha muscle tissue, chrondrichthyes muscle tissue, osteichthyes muscle tissue, and caprine muscle tissue, (vii) the system further comprises means for affecting at least one of: osmotic stress, and fluid stress, (viii) the means for affecting osmotic stress comprises contacting the at least one resilient container with a membrane containing an agent with a higher chemical potential than the tissue culture at any given time, (ix) wherein the means for affecting fluid stress comprises a tube affecting fluid communication between two resilient containers, wherein (x) the inkjet bioprinting module is configured to provide the tissue culture, (xi) the tissue culture further comprises a biocompatible scaffolding configured to deliver nutrients to the tissue scaffolding bulk, wherein (xii) the at least one resilient container is coated with a material configured promote adhesion between the tissue culture and the resilient container, wherein (xiii) the biocompatible scaffolding comprises: PEGilated-methacrylate, chitosan, carrageenan, poly (lactic) acid, poly(lactic-co-glycolic acid), their methacrylate conjugates, co-polymers, interpenetrating networks or a composition comprising one or more of the foregoing, (xiv) the first bio-ink comprises one or more of endothelial cells, muscle cells, fibroblast cells, mesothelial cells, pericyte cells, monocyte cells, plasma cells, mast cells, adipocyte cells, chondrocyte cells, cells population manipulated from a specific type of cell to another, or cells composition comprising one or more of the foregoing cells; a bio-compatible polymer; and optionally a photoinitiator, wherein (xv) the second bio-ink comprises extracellular material (ECM), (xvi) the ECM is comprises epidermal growth factor (EGF), basic fibroblast growth factor (bFGF), bone morphogenic protein (BMP), insulin-like growth factor (IGF), glucoseaminoglycan (GAG), Transforming growth factor (TGF) or extracellular matrix compound composition comprising the foregoing, wherein the method further (xvii) comprising admixing biocompatible pellets to the at least one resilient container, configured to impose a predetermined shape to at least a portion of the tissue culture, further comprising (xviii) a step of transferring the physically manipulated tissue culture to an incubator; and growing the tissue culture, and wherein (xix) the system further comprises a housing operable to accommodate a plurality of resilient containers disposed in a structure operable to simultaneously, at predetermined intervals, based on the physical data characteristic of the tissue culture in the plurality of resilient containers, affect at least one of the same: stress, and strain on the plurality of resilient containers.

Although the foregoing disclosure for mechanically or manually (or both) physically manipulating a resilient container of bioprinted tissue culture having non-random three dimensional cell structure over 4 dimensions has been described in terms of some exemplary implementations, other exemplary implementations will be apparent to those of ordinary skill in the art from the disclosure herein. Moreover, the described exemplary implementations have been presented by way of example only, and are not intended to limit the scope of the inventions. Indeed, the novel methods, programs, libraries and systems described herein may be embodied in a variety of other forms without departing from the spirit thereof. Accordingly, other combinations, omissions, substitutions and modifications will be apparent to the skilled artisan in view of the disclosure herein.

What is claimed:

1. A method of physically manipulating a tissue culture, implementable in a computerized system comprising: at least one resilient container operably coupled to a frame sized and configured to affect a predetermined regimen of stress and strain over at least one of four degrees of freedom on the at least one resilient container, and a central processing module (CPM) in communication with at least one processor and at least one non-volatile memory storage device having thereon a processor readable media with a set of executable instructions, configured, when executed, to cause the at least one processor to:
using a sensor array included with the system, receive physical data characteristic of the tissue culture; and based on the data, physically manipulate the at least one resilient container, the method comprising:
 a. loading the tissue culture into the at least one resilient container; and
 b. at predetermined intervals, based on the physical data characteristic of the tissue culture, affect at least one of stress, and strain on the at least one resilient container.

2. The method of claim 1, wherein the system further comprises an ink jet bioprinting module having
 a. at least one microprocessor in communication with: a non-volatile storage device having thereon a microprocessor-readable medium with a set of executable instructions configured to, when executed, to cause the at least one microprocessor to execute a method of inkjet bioprinting; and an image library corresponding to a two dimensional (2D) layer of at least one of cells, scaffolding, and connective tissue within a biostructure having a predetermined three dimensional (3D) pattern of cells therein;
 b. a first dispensing print head in communication with the microprocessor having: at least one aperture, a first bio-ink reservoir, and a first dispenser configured to dispense the first bio-ink through the aperture, wherein the first bio-ink is a composition comprising viable cells suspended in a bio-compatible dispersing medium, and/or a bio-compatible polymer, and/or a bio-compatible monomer, and/or a bio-compatible oligomer;
 c. a second dispensing print head in communication with the microprocessor having:
 at least one aperture, a second bio-ink reservoir, and a second dispenser configured to dispense the second bio-ink through the aperture, wherein the second bio-ink is a composition of:
 biocompatible compounds suspended in a bio-compatible dispersing medium, and/or the bio-compatible polymer, and/or the bio-compatible monomer, and/or the bio-compatible oligomer;
 d. a third dispensing print head in communication with the microprocessor having:
 at least one aperture, a third bio-ink reservoir, and a third dispenser configured to dispense the third bio-ink through the aperture, wherein the third bio-ink comprises means for functionalizing the bio-compatible polymer, the bio-compatible monomer, or the bio-compatible oligomer; and
 e. a conveyor in communication with the microprocessor, operably coupled to each of the first, the second, and the third dispensing print heads.

3. The method of claim 1, wherein the four degrees of freedom are configured to compress, elongate, shear and apply torque to the tissue culture in the at least one resilient container.

4. The method of claim 3, wherein the physical characteristic is at least one of: viscosity, density, weight, opacity, specific volume, relative water activity, pH, tensile strength, and compressive strength.

5. The method of claim 4, wherein the sensor array comprises at least one of: a timer, a viscometer, a load cell, an actinic radiation source, a camera, and a hygrometer.

6. The method of claim 5, wherein the tissue culture is configured to emulate a bovine muscle tissue, a porcine muscle tissue, an avian muscle tissue, a gnatha muscle tissue, chrondrichthyes muscle tissue, osteichthyes muscle tissue, and caprine muscle tissue.

7. The method of claim 1, wherein the system further comprises means for affecting at least one of: osmotic stress, and fluid stress.

8. The method of claim 7, wherein the means for affecting osmotic stress comprises contacting the at least one resilient container with a membrane containing an agent with a higher chemical potential than the tissue culture at any given time.

9. The method of claim 7, wherein the means for affecting fluid stress comprises a tube affecting fluid communication between two resilient containers.

10. The method of claim 2, wherein the inkjet bioprinting module is configured to provide the tissue culture.

11. The method of claim 10, wherein the tissue culture further comprises a biocompatible scaffolding.

12. The method of claim 10, wherein the at least one resilient container is coated with a material configured promote to promote adhesion between the tissue culture and the resilient container.

13. The method of claim 11, wherein the biocompatible scaffolding comprises: PEGylated-methacrylate, chitosan, carrageenan, poly(lactic) acid, poly(lactic-co-glycolic acid), their methacrylate conjugates, co-polymers, interpenetrating networks or a composition comprising one or more of the foregoing.

14. The method of claim 13, wherein the first bio-ink comprises one or more of: endothelial cells, muscle cells, fibroblast cells, mesothelial cells, pericyte cells, monocyte cells, plasma cells, mast cells, adipocyte cells, chondrocyte cells, or cell composition comprising one or more of the foregoing cells; and the bio-compatible polymer.

15. The method of claim 10, wherein the second bio-ink comprises extracellular material (ECM).

16. The method of claim 15, wherein the ECM comprises epidermal growth factor (EGF), basic fibroblast growth factor (bFGF), bone morphogenic protein (BMP), insulin-like growth factor (IGF), glycosaminoglycan (GAG), Transforming growth factor (TGF) or extracellular matrix compound composition comprising the foregoing.

17. The method of claim 1, further comprising admixing biocompatible pellets to the at least one resilient container, configured to impose a predetermined shape to at least a portion of the tissue culture.

18. The method of claim 17, further comprising a step of transferring the physically manipulated tissue culture to an incubator; and growing the tissue culture.

19. The method of claim 18, wherein the system further comprises a housing operable to accommodate a plurality of resilient containers disposed in a structure operable to simultaneously, at predetermined intervals, based on the physical data characteristic of the tissue culture in the plurality of resilient containers, affect at least one of the same: stress, and strain on the plurality of resilient containers.

* * * * *